(12) United States Patent
Hackenberg et al.

(10) Patent No.: US 6,728,643 B2
(45) Date of Patent: Apr. 27, 2004

(54) PROCESS AND DEVICE FOR MEASURING THE CONCENTRATIONS OF A PLURALITY OF GAS COMPONENTS IN A GAS SAMPLE

(75) Inventors: Michael Hackenberg, Lübeck (DE); Matthias Studer, Krummesse (DE)

(73) Assignee: Drägerwerk Aktiengesellschaft, Lubeck (DE)

( * ) Notice: Subject to any disclaimer, the term of this patent is extended or adjusted under 35 U.S.C. 154(b) by 8 days.

(21) Appl. No.: 10/170,741

(22) Filed: Jun. 13, 2002

(65) Prior Publication Data

US 2003/0041648 A1 Mar. 6, 2003

(30) Foreign Application Priority Data

Aug. 21, 2001 (DE) ......................................... 101 40 945

(51) Int. Cl.[7] .............................................. G01N 31/00
(52) U.S. Cl. ........................... 702/24; 702/22; 702/104; 73/1.02; 204/424
(58) Field of Search ........................... 702/24, 22, 104; 73/31.05, 1.06, 23.31, 31.02, 25.03, 1.02, 101, 23.2; 204/425, 426, 427, 415, 433, 424

(56) References Cited

U.S. PATENT DOCUMENTS

| | | | | |
|---|---|---|---|---|
| 5,763,760 A | * | 6/1998 | Gumbrecht et al. | 73/1.06 |
| 6,037,178 A | * | 3/2000 | Leiner et al. | 436/50 |
| 6,066,249 A | * | 5/2000 | Manzoni et al. | 205/782 |
| 6,196,053 B1 | * | 3/2001 | Kato et al. | 73/31.05 |
| 6,266,998 B1 | * | 7/2001 | Hackenberg | 73/31.05 |

FOREIGN PATENT DOCUMENTS

DE   196 22 931 A1   12/1997

\* cited by examiner

*Primary Examiner*—John Barlow
*Assistant Examiner*—Hien Vo
(74) *Attorney, Agent, or Firm*—McGlew and Tuttle, P.C.

(57) ABSTRACT

A process and device measures and checks concentration values of a plurality of gas components in a gas sample. The distortion of the measuring results by temperature and moisture effects, contamination as well as cross sensitivity and drift phenomena of the sensors of the gas-measuring device is a frequent problem in the measurement of gases by a gas-measuring device. It is possible with the process to recognize implausible measuring results as such on the gas-measuring device without design measures. This is achieved by the evaluation of data of suitably selected calibrating gases, from which a subvector space is constructed in the vector space of all possible measurement data $(s_1, s_2, s_3)$, represented as a plane (E), and a corresponding tolerance range is constructed. If the data (*) determined later during a measurement, are in the tolerance range, they are classified as plausible, and otherwise as implausible. The subvector space is constructed, e.g., such that the sum of the distances of the measurement points belonging to the calibrating gases from the subvector space is as small as possible.

21 Claims, 2 Drawing Sheets

PROCESS AND DEVICE FOR MEASURING THE CONCENTRATIONS OF A PLURALITY OF GAS COMPONENTS IN A GAS SAMPLE

FIELD OF THE INVENTION

The present invention pertains to a process for measuring and checking concentration values of a plurality of gas components in a gas sample.

BACKGROUND OF THE INVENTION

A gas-measuring device with a plurality of sensors, which are provided for the measurement of the gas components to be expected and whose measuring sensitivity is selected correspondingly, is used, in general, for the measurement in a gas sample. The gas sample consists of individual gas components, which are simultaneously detected by the sensors.

A frequent problem in gas measurement by means of the prior-art gas-measuring device is the insufficient selectivity. This means that the sensors have cross sensitivities for other gas components besides the desired sensitivity for the particular gas component to be measured. The occurrence of other gas components, with respect to which a sensor has cross sensitivity, leads to distorted measuring results, which cannot be compensated if they are not recognized as such. Additional distortions of the measuring results occur, e.g., due to variations in temperature, moisture effects, contamination of the gas-measuring device, aging-related sensitivity drift and zero drifts of the sensors.

One possibility of recognizing such disturbing effects on electrochemical gas sensors during the measurement of concentration values of gas components in a gas sample and of compensating them as a result is to use an additional measuring electrode. An electrochemical multiple-gas sensor, with which different gas components in one gas sample are detected simultaneously, is described in DE 196 22 931 A1. A measuring electrode for hydrogen sulfide, which consists of gold, iridium and carbon or graphite and is to detect a cross sensitivity of the other measuring electrodes to hydrogen sulfide, is additionally provided there.

SUMMARY OF THE INVENTION

The process according to the present invention represents a further improvement besides the use of an additional measuring electrode in an electrochemical gas sensor for recognizing disturbing effects. The process can also be applied to gas sensors that are based on different principles of measurement, e.g., infrared optical gas sensors, semiconductor gas sensors or catalytic heat tone gas sensors.

The object of the present invention is to provide a process with which the occurrence of disturbing effects due to a great variety of causes, e.g., temperature variations, moisture, contamination, as well as drift phenomena, can be recognized on the sensors.

A gas-measuring device with n sensors, where n is the number of sensors and m n equals at least 2, is used for the process for measuring and subsequently checking concentration values of gas components in a gas sample. Furthermore, the gas-measuring device comprises an evaluating unit, which receives and evaluates the values measured and passed on by the n sensors.

A plurality of different calibrating gases are introduced into the gas-measuring device with the n gas sensors for measuring the concentrations of m<n possible gas components.

Gases that comprise the gas components that are later taken into consideration during the measurement in the gas sample are used as calibrating gases. Gases that comprise a single possible gas component are advantageously used as calibrating gases; this leads to m different possibilities, but it is also possible to use gases that comprise a combination of two possible gas components, in which case an additional $m(m-1)/2$ possibilities arise. Thus, $m+m(m-1)/2=m(m+1)/2$ different calibrating gases are obtained, whose number is now large enough to guarantee a reliable calibration.

The corresponding n measured values of the n sensors are passed on to the evaluating unit for each calibrating gas.

The measured values of a calibrating gas form an n-dimensional measurement point, which can be considered to be the vector in the n-dimensional vector space of all possible measured value configurations from n measured values. The number of measurement points thus obtained equals the number of calibrating gases selected. An m-dimensional subvector space is sought for these measurement points in the n-dimensional vector space of all possible measurement points, i.e., of all possible measured value configurations, which comprises in the best approximation all measurement points of the calibrating gases. This is to be understood such that a subvector space is constructed, e.g., such that the sum of the distances between the measurement points belonging to the calibrating gases and the subvector space is as small as possible. A tolerance range, which surrounds the subvector space, is determined for the subvector space. No restricting conditions are attached, in principle, to the tolerance range. However, the tolerance range is preferably selected to be such that it comprises the measurement points whose distance from the subvector space can still be explained with the usual measurement inaccuracies, i.e., noises. In light of the evaluation by calculation, it is advantageous to set the tolerance range as the range of the measurement points in the vector space of all possible measurement points whose distance from the subvector space determined is below a preset fixed distance value.

After the conclusion of the calibration operation, the gas sample is introduced into the gas-measuring device, and n values, which will yield an n-dimensional measurement point, are measured by means of the n sensors.

If this measurement point is located within the tolerance range, it is classified by the evaluating unit as plausible; if the measurement point is located outside the tolerance range, it is classified by the evaluating unit as implausible.

An essential feature of the process is based on the fact that the measured value configurations are considered to be measurement points in a vector space, because simple criteria can thus be formulated by calculation, by means of which criteria it can be decided whether the measurement point belonging to a gas sample is to be classified as plausible, i.e., as a measurement point that has a sufficiently short distance from the set of the measurement points in the vector space, which are obtained from the calibration data, or whether the measurement point belonging to the gas sample is to be classified as implausible, i.e., as a measurement point that is located at an excessively great distance from the set of measurement points obtained from the calibration data. How a "set of measurement points" and how a "distance" are to be selected is obvious from the vector space structure. The advantage of the process is that immediately after a measurement and with comparatively simple methods, a measuring result can be discarded if it is to be considered to be implausible based on the measured values. This would be the case, e.g., when one of the sensors measures a greatly increased value that is unrealistic in connection with the other values due to its cross sensitivity to a gas component not taken into account during the calibration. Such an example is a sensor that is defective and hardly responds, so that only extremely low values are measured. The evaluating unit classifies the corresponding measurement point as implausible in both cases, and the user can track down the cause of the disturbing effect.

Electrochemical gas sensors are used as the sensors in a preferred embodiment.

A design of the process with n=3 sensors and m=2 possible gas components is of particular significance for practice. These are, e.g., chlorine ($Cl_2$) and sulfur dioxide ($SO_2$). The concentrations of the possible gas components chlorine and sulfur dioxide can thus be determined in one gas sample after the conclusion of the calibration operation, and implausible measuring results are immediately recognized and their cause can be explored.

If a measurement point has been classified by the evaluating unit as plausible or implausible, this result is communicated in a preferred embodiment to the user via a display unit. In case of implausible measurement points, it would be possible, e.g., to send a warning to the user.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
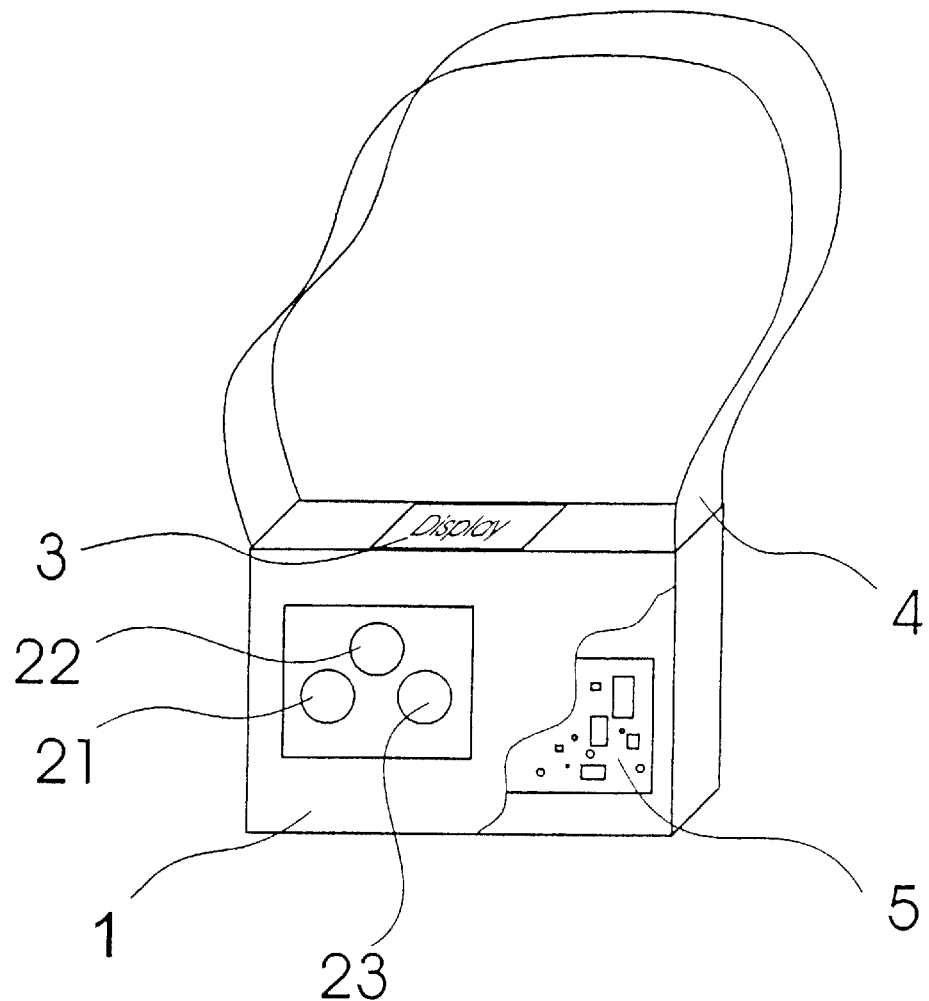
FIG. 1 is a gas-measuring device, with which the process according to the present invention can be carried out.

Referring to the drawings in particular the gas-measuring device shown in FIG. 1 comprises a portable housing 1 with a carrying strap 4. Three electrochemical gas sensors 21, 22 and 23, which are used to measure the concentrations of possible gas components in the gas, axe located in the housing 1. The sensor 21 is a Dräger-XS EC $Cl_2$ type sensor and it sensitively responds to chlorine ($Cl_2$); sensor 22 is a Dräger-XS $SO_2$ type sensor and it sensitively responds to sulfur dioxide ($SO_2$), and sensor 23 is a Dräger-EC $Cl_2$ type sensor and it likewise measures the concentration of chlorine ($Cl_2$), but it has, on the whole, different cross sensitivities than the sensor 21. The concentration values measured by the sensors 21, 22 and 23 are sent to an evaluating unit 5 integrated within the gas-measuring device. The optionally processed concentration values and the result of a plausibility checking of the measuring results by the evaluating unit 5 are sent from there to the display unit 3.

The plausibility checking of the concentration values for chlorine and sulfur dioxide as they were measured by the sensors 21, 22 and 23 will be described below.

A linear relationship is first assumed between the signals received from the sensors 21, 22 and 23 and the concentration values of the gas components chlorine and sulfur dioxide. This condition is the basis for the following statement:

$$c = s \cdot A$$

with $c=(c_1, c_2)$ as the vector with the chlorine concentration $c_1$ and with the sulfur dioxide concentration $c_2$. The symbol $s=(s_1, s_2, s_3)$ designates the vector with the signal $s_1$ received from the sensor 21, with the signal $s_2$ received from the sensor 22 and with the signal $s_3$ received from the sensor 23.

Since the relationship between the vector c of the concentration values and the vector s of the received signals is assumed to be linear, it can be represented by a 2×3 matrix $$A = \begin{pmatrix} a_{11} & a_{12} \\ a_{21} & a_{22} \\ a_{31} & a_{32} \end{pmatrix}$$

whose coefficients have yet to be determined.

The coefficients $a_{11}, a_{12}, a_{21}, a_{22}, a_{31}$ and $a_{32}$ of the matrix A are determined by the calibration.

Five different calibrating gases, which are characterized by a vector $c=(c_1, c_2)$ with the chlorine concentration $c_1$ and with the sulfur dioxide concentration $c_2$, are introduced in this case. The five vectors of the different calibrating gases together yield a 2×5 matrix C, which contains the following values:

$$C = \begin{pmatrix} 0 & 1 \\ 1 & 0 \\ 1 & 1 \\ 0.2 & 0.8 \\ 0.7 & 0.3 \end{pmatrix}$$

The first line of matrix C corresponds to a calibrating gas containing 1 ppm (parts by million) of sulfur dioxide, and the second line corresponds to a calibrating gas containing 1 ppm of chlorine. The third through fifth lines correspond to calibrating gases containing 1 ppm of chlorine and 1 ppm of sulfur dioxide, 0.2 ppm of chlorine and 0.8 ppm of sulfur dioxide, and 0.7 ppm of chlorine and 0.3 ppm of sulfur dioxide.

The gases advantageously used as calibrating gases are gases that comprise one of the two possible gas components chlorine and sulfur dioxide, as well as gases that comprise a combination of the two possible gas components chlorine and sulfur dioxide. In the latter case, additional calibrating gases are obtained in a meaningful manner by taking into account different concentration ratios when combining the two gas components, namely, 1 ppm—1 ppm, 0.2 ppm–0.8 ppm, and 0.7 ppm–0.3 ppm.

A vector $s=(s_1, s_2, s_3)$ with the signal $s_1$ received from the sensor 21, with the signal $s_2$ received from the sensor 22, and with the signal $s_3$ received from the sensor 23 belongs to each calibrating gas.

If the vectors s of the received signals, which vectors belong to a vector c each with the concentrations of a calibrating gas, are combined, the 3×5 matrix $$S = \begin{pmatrix} -0.1261 & 0.9795 & -1.0860 \\ 1.0402 & -0.3653 & 1.0447 \\ 0.8776 & 0.6186 & -0.0689 \\ 0.1003 & 0.7168 & -0.6393 \\ 0.6836 & 0.0331 & 0.3762 \end{pmatrix}$$

is obtained.

The relationship $$C = S \cdot A$$

applies with the 2×5 matrix C, which contains as the coefficients the concentrations of chlorine and sulfur dioxide in the calibrating gases, with the 3×5 matrix S, which contains as the coefficients the sensor signals received, and with the 2×3 matrix A with initially still unknown coefficients. A total of 10 scalar equations are obtained from the matrix equation C=S·A for the 6 unknown coefficients $a_{11}$, $a_{12}$, $a_{21}$, $a_{22}$, $a_{31}$, $a_{32}$. Thus, this set of equations is overdetermined. A solution is therefore determined by means of the least-squares methods such that the matrix equation C=S·A will be satisfied in the best approximation.

The following values are obtained in the example:

$$A = \begin{pmatrix} 1.0340 & 0.5052 \\ 0.1234 & 0.8723 \\ -0.0186 & -0.1953 \end{pmatrix}.$$

It is thus possible to calculate the concentrations of the gas components chlorine and sulfur dioxide, which are integrated in a vector $c=(c_1, c_2)$, from the signals received from the sensors 21, 22 and 23, which signals are integrated in a vector $s=(s_1, s_2, s_3)$.

However, the concentrations $c=(c_1, c_2)$ shall be determined only for plausible measurement points $s=(s_1, s_2, s_3)$.

A two-dimensional subvector space, which comprises all the measurement points determined for the calibrating gases in the best approximation, is determined for this below in the three-dimensional vector space of all possible measurement points $s=(s_1, s_2, s_3)$. The two principal axes, at which the greatest deviations exist between the measurement points determined for the calibrating gases, are determined for the 3×5 matrix S with the methods of linear algebra. These two principal axes (0.3947; −0.5074; 0.7660) and (0.8233; 0.5654; −0.0497) define the two-dimensional subvector space being sought.

Figure 2:
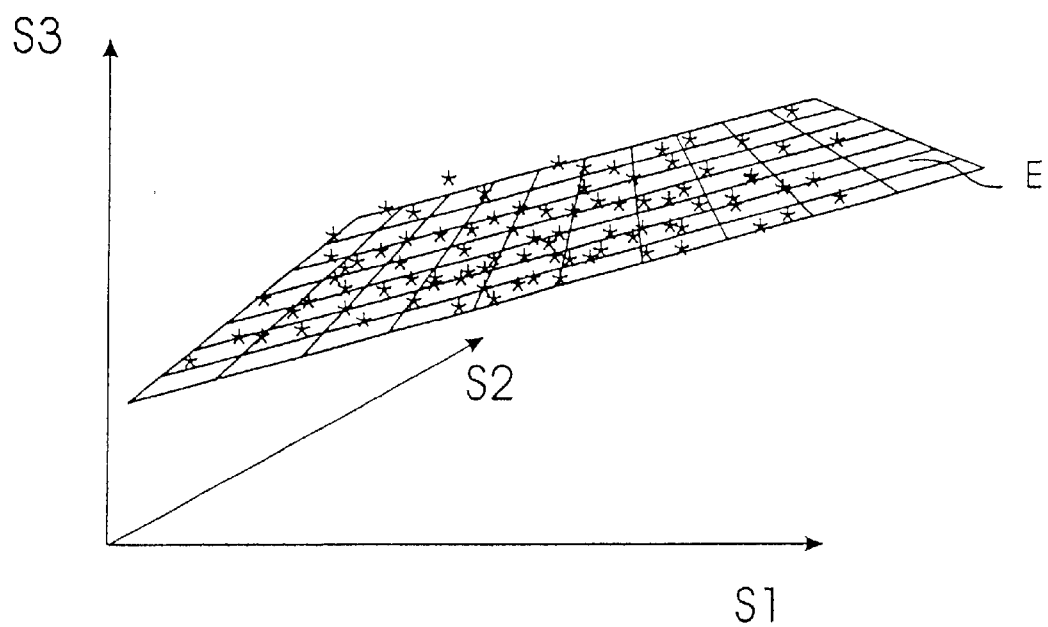
FIG. 2 is a two-dimensional subvector space in the three-dimensional vector space of all possible measurement points as well as measurement points determined by means of three sensors.

The two-dimensional subvector space being sought is shown in FIG. 2 in the three-dimensional vector space of all possible measurement points as a plane E. Numerous measurement points in plane E or in the vicinity of plane E, which are not specified more closely, are indicated as asterisks.

A distance of a value of 0.05, which is selected based on the average distance between the vectors s of the calibrating gases and the subvector space E, which can be explained by the usual measuring inaccuracies, is determined for the two-dimensional subvector space E.

The plausibility checking is now demonstrated on the basis of the example of a gas sample with a concentration value of 0.4 ppm for chlorine and a concentration value of 0.6 ppm for sulfur dioxide. s=(0.3284; 0.4365; −0.2333) is obtained as the vector in a first unaffected measurement; s=(0.3169; 1.1817; −0.2557) is obtained as the vector in a second measurement with an additional interfering gas ($H_2S$) at a concentration of 0.2 ppm; and s=(0.3162; 0.2230; −0.2388) is obtained as the vector in a third measurement with a defective sensor 22, which has a 50% loss of sensitivity.

The distance of s from the subvector space E is 0.0004 in the first case and is smaller than the preset distance of 0.05. Consequently, the measurement point is in the tolerance range and is classified by the evaluating unit 5 as plausible. The distance of s from the subvector space E is 0.4753 in the second case and is greater than the preset distance of 0.05. The distance of s in the third case, equaling 0.1371, is likewise greater than 0.05. The measurement points are thus outside the tolerance range in the latter two cases and are classified by the evaluating unit 5 as implausible.

This reflects the actual conditions, in which the interfering gas hydrogen sulfide leads to deviations of the concentrations determined from the sensor signals from the actual concentrations by up to 100% or more in the second case, and the defective sensor 22 leads to deviations of the concentrations determined from the sensor signals from the actual concentrations by more than 30% in the third case.

While specific embodiments of the invention have been shown and described in detail to illustrate the application of the principles of the invention, it will be understood that the invention may be embodied otherwise without departing from such principles.

What is claimed is:

1. A process for measuring and checking concentration values of a plurality of gas components in a gas sample, the process comprising the steps of:

introducing a plurality of different calibrating gases into a gas-measuring device with a plurality of sensors, where "n" represents the number of the plurality of sensors, said sensors are for measuring a plurality of possible gas components, where "m" represents the number of possible gas components, the number of sensors "n" and the number of possible gas components "m" have the relationship of m<n;

passing a corresponding n number of measured values for each calibrating gas, as measurement points, on to an evaluating unit;

determining a "m" number-dimensional subvector space, which comprises in the best approximation all the measurement points determined for the measurement points determined for the calibrating gases in an n-dimensional vector space of all possible measurement points;

determining a tolerance range, which forms the environment of the m-dimensional subvector space (E) in the n-dimensional vector space of all possible measurement points;

introducing a gas sample into the gas-measuring device;

passing corresponding measurement points determined by the sensors for the gas sample to the evaluating unit;

classifying, with the evaluating unit, each measurement point determined for the gas sample within the tolerance range as plausible, and classifying, with the evaluating unit, each measurement point located outside the tolerance range as implausible.

2. A process in accordance with claim 1, wherein the calibrating gases introduced comprise at least m number gases individually with one of the m number of possible gas components, as well as m(m−1)/2 gases with one of the m(m−1)/2 possible combinations of two different of the m possible gas components.

3. A process in accordance with claim 1, wherein said subvector space (E) determined in the best approximation is determined such that the sum of the distances of the measurement points determined for the calibrating points from the subvector space is as small as possible.

4. A process in accordance with claim 2, wherein said subvector space (E) determined in the best approximation is determined such that the sum of the distances of the measurement points determined for the calibrating points from the subvector space is as small as possible.

5. A process in accordance with claim 1, wherein said sensors are electrochemical gas sensors.

6. A process in accordance with claim 1, wherein the tolerance range comprises all the measurement points in the vector space that have at most a fixed, preset distance from the subvector space.

7. A process in accordance with claim 1, wherein n=3 and the three sensors are used for m=2 possible gas components.

8. A process in accordance with claim 1, further comprising reporting to the user via a display unit whether the measurement point determined for the gas sample is classified by said evaluating unit as plausible or not.

9. A process for measuring and checking concentration values of a plurality of gas components in a gas sample, the process comprising the steps of:
   providing a gas-measuring device with a plurality of sensors for measuring a plurality of possible gas components, where the number of components to be measured is less than the number of sensors;
   introducing different calibrating gases to the gas-measuring device to generate measured values;
   evaluating the measured values for each calibrating gas to determine a subvector space having a number of dimensions equal to the number of components to be measured, the subvector space comprising a best approximation of all the measurement values determined for the calibrating gases in a vector space of all possible measurement values having a number of dimensions equal to the number of sensors;
   determining a tolerance range, which forms the environment of the subvector space in the vector space of all possible measurement values;
   introducing a gas sample into the gas-measuring device to generate sample measured values;
   evaluating the sample measured values to classify measured values within the tolerance range as plausible, and to classify measured values located outside the tolerance range as implausible.

10. A process in accordance with claim 9, wherein the calibrating gases comprise single gas component gases and at least one gas having two gas components.

11. A process in accordance with claim 9, wherein said subvector space determined in the best approximation is determined such that the sum of the distances of the measurement points determined for the calibrating points from the subvector space is as small as possible.

12. A process in accordance with claim 10, wherein said subvector space determined in the best approximation is determined such that the sum of the distances of the measurement points determined for the calibrating points from the subvector space is as small as possible.

13. A process in accordance with claim 9, wherein said sensors are electrochemical gas sensors.

14. A process in accordance with claim 9, wherein the tolerance range comprises all the measurement points in the vector space that have at most a fixed, preset distance from the subvector space.

15. A process in accordance with claim 9, wherein three sensors are used for 2 possible gas components.

16. A process in accordance with claim 9, further comprising reporting to the user via a display unit whether the measurement point determined for the gas sample is classified by said evaluating unit as plausible or not.

17. A gas measuring device for measuring and checking concentration values of a plurality of gas components in a gas sample, the device comprising:
   a plurality of sensors for measuring a plurality of possible gas components, where the number of components to be measured is less than the number of sensors;
   calibrating gases to generate measured values;
   an evaluation unit for evaluating the measured values for each calibrating gas to determine a subvector space having a number of dimensions equal to the number of components to be measured, the subvector space comprising a best approximation of all the measurement values determined for the calibrating gases in a vector space of all possible measurement values having a number of dimensions equal to the number of sensors and for determining a tolerance range, which forms the environment of the subvector space in the vector space of all possible measurement values and upon introducing a gas sample into the gas-measuring device to generate sample measured values evaluating the sample measured values to classify measured values within the tolerance range as plausible, and to classify measured values located outside the tolerance range as implausible; and
   a display unit for displaying whether the measurement point determined for the gas sample is classified by said evaluating unit as plausible or not.

18. A device in accordance with claim 17, wherein the calibrating gases comprise single gas component gases and at least one gas having two gas components.

19. A device in accordance with claim 17, wherein said sensors are electrochemical gas sensors.

20. A device in accordance with claim 17, wherein three sensors are used for 2 possible gas components.

21. A process in accordance with claim 1, wherein:
   a number of said plurality of calibration gases is equal to or greater than the number of gas components, each of said calibration gases includes one of said gas components, said plurality of calibration gases include a subset of calibration gases, each gas of said subset has different combinations of two of said gas components.

* * * * *